(12) United States Patent
Fine et al.

(10) Patent No.: US 9,408,889 B2
(45) Date of Patent: Aug. 9, 2016

(54) FUSION PEPTIDE DESIGNED TO REDUCE PLAQUE BACTERIA AND YEAST IN THE ORAL CAVITY

(75) Inventors: Daniel H. Fine, New York, NY (US); Kabilan Velliyagounder, Monmouth Junction, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/113,245

(22) PCT Filed: Apr. 23, 2012

(86) PCT No.: PCT/US2012/034705
§ 371 (c)(1),
(2), (4) Date: Feb. 7, 2014

(87) PCT Pub. No.: WO2012/145758
PCT Pub. Date: Oct. 26, 2012

(65) Prior Publication Data
US 2014/0194344 A1    Jul. 10, 2014

Related U.S. Application Data

(60) Provisional application No. 61/478,369, filed on Apr. 22, 2011, provisional application No. 61/586,449, filed on Jan. 13, 2012.

(51) Int. Cl.
*A61K 38/16* (2006.01)
*A61K 45/06* (2006.01)
*C07K 14/00* (2006.01)
*A23L 1/305* (2006.01)
*C07K 14/79* (2006.01)
*C07K 14/21* (2006.01)
*A61K 38/00* (2006.01)

(52) U.S. Cl.
CPC ............... *A61K 38/16* (2013.01); *A23L 1/3053* (2013.01); *A61K 45/06* (2013.01); *C07K 14/001* (2013.01); *C07K 14/21* (2013.01); *C07K 14/79* (2013.01); *A61K 38/00* (2013.01); *C07K 2319/00* (2013.01)

(58) Field of Classification Search
CPC ...... A23L 1/3053; A61K 38/00; A61K 38/16; A61K 45/06; C07K 14/001; C07K 14/21; C07K 14/79; C07K 2319/00
See application file for complete search history.

(56) References Cited

U.S. PATENT DOCUMENTS

2008/0287367 A1 * 11/2008 Hodges et al. .................. 514/13
2010/0144598 A1    6/2010 Fine et al.

FOREIGN PATENT DOCUMENTS

| WO | WO 9212169 A1 * | 7/1992 | ............... C07K 7/06 |
| WO | 2007089272 A2 | 8/2007 | |
| WO | WO 2008089234 A2 * | 7/2008 | ............. A61K 38/40 |
| WO | WO 2010080819 A1 * | 7/2010 | ............. A61K 38/00 |

OTHER PUBLICATIONS

Atsuo Amano, Binding Sites of Salivary Statherin for Porphyromonas gingivalis Recombinant Fimbrillin, Infection and Immunity, Oct. 1996, p. 4249-4254.*
Raj et al. Salivary Statherin: Dependence on Sequence, Charge, Hydrogen Bonding Potency, and Helical Conformation for Adsorption to Hydroxyapatite and Inhibition of Mineralization. J. Bioi. Chem. 267(9): 5968-5976. (1992).
Kelly, G., A snythetic peptide adhesion epitope as a novel antimicrobial agent, Nature Biotechnology 17: 42-47. (1999).

* cited by examiner

*Primary Examiner* — James H Alstrum Acevedo
*Assistant Examiner* — Erinne Dabkowski
(74) *Attorney, Agent, or Firm* — Fox Rothschild LLP (57) ABSTRACT

The present invention relates generally to dental diseases, caries and periodontal disease. More specifically, the invention relates to Lactoferrin and PAK fusion peptides (PAK-LF), along with therapeutic, diagnostic and research uses for these polypeptides. The present invention also provides methods of treating dental diseases, caries and periodontal disease.

19 Claims, 6 Drawing Sheets

Figure 1

A1-PBS A2-BEC A3-PAK A4-PAKLF

B1-PBS B2-BEC B3-PAK B4-PAKLF

C1-PBS C2-BEC C3-PAK C4-PAKLF

A- BEC protein, PAK and Lf-PAK peptides-Control (peptides taken for experiment)

B-Release of different peptides from BEC after 4 hrs of incubation

C-Supernatant of different peptides incubated with BEC for one hour (remaining unbound peptides)

FUSION PEPTIDE DESIGNED TO REDUCE PLAQUE BACTERIA AND YEAST IN THE ORAL CAVITY

RELATED APPLICATIONS

This application is the U.S. National Phase of International Patent Application Serial No. PCT/US2012/034705, filed Apr. 23, 2012, which claims priority to U.S. Provisional Application Nos. 61/478369, filed, Apr. 22, 2011, and 61/586,449, filed Jan. 13, 2012, the disclosures of which are hereby incorporated by referenced in their entireties.

STATEMENT REGARDING FEDERALLY SPONSORED RESEARCH OR DEVELOPMENT

This invention was made with government support under grant nos. R21-DE16474, R01-DE017968, and 3R01-DE017968 awarded by National Institutes of Health (NIH). The government has certain rights in the invention.

BACKGROUND OF THE INVENTION

For many years, researchers have attempted to develop chemotherapeutic agents that could be useful in combating infections in the oral cavity. As far back as the mid-1940's, with the introduction of antibiotics it became clear that although these potent agents had the potential to be effective, problems unique to the oral cavity interfered with their utility. As time went on bacterial plaque development in the oral cavity became better understood. With that better understanding it became clear that agents delivered to the oral cavity needed to adhere to oral tissues to resist removal by the flows of saliva and the forces of oral mastication. It became widely accepted that for antimicrobial agents to be effective in the oral cavity the agent(s) needed to be sustained in that environment over time. One experiment that illustrates this principle compared the efficacy of two prominent antimicrobial agents, tetracycline and penicillin. Penicillin was shown to be a more potent agent as compared to tetracycline when tested in-vitro. As such it was shown that Penicillin was effective against oral bacteria at a significantly lower concentration as compared to tetracycline when tested against bacteria grown in a broth media (1 ug/ml for Penicillin vs. 10-20 ug/ml for Tetracycline). Further, Penicillin is a bactericidal agent and thus promotes killing of bacteria, while tetracycline is bacteriostatic and thus slows bacterial growth and development. Nonetheless, in spite of these dramatic differences in potency, tetracycline proves to be a more effective anti-microbial agent when applied topically in the oral cavity. Thus when tetracycline was added to a salivary coated hydroxylapatite disk (SHA), a surrogate for the tooth/enamel surface, and then this tetracycline treated SHA tooth homologue was washed and then placed in a culture of bacteria it was seen that very few of these organisms were able to adhere to SHA. On the other hand when the SHA was treated in a similar manner with Penicillin there was no effect. Thus in spite of tetracycline's reduced potency when compared to Penicillin, tetracycline was superior in an assay that accounted for adherence and release of a drug from a salivary coated tooth analogue. Since the two most common dental diseases, caries and periodontal disease, result from oral bacteria that stick to the tooth surface, tests for antimicrobial efficacy in the oral cavity need to focus on ways to prevent or reduce bacteria from attaching to the tooth surfaces.

With that understanding, research in the late 1960's and early 1970's examined agents with the characteristic of substantivity, the ability of an agent to bind to and be released from a tooth-like surface. One of the first agents studied that possessed this characteristic was chlorhexidine, a bisbiguanide antimicrobial, that was shown both in vitro and in vivo to reduce bacterial plaque attachment to teeth. Agents known as Peridex® and Perioguard® were investigated and are currently commercially available oral mouth rinse agents that have been tested and shown to bind to the oral tissues. This property of substantivity combined with antimicrobial activity results in reduction in both gingivitis and caries levels when used in clinical studies. Since that time there have been many attempts to develop agents that work effectively in the oral cavity. Thus far clinical testing has demonstrated very few successes. One such success has utilized the agent, triclosan, the active ingredient in Colgate Total® toothpaste. This dentifrice has been tested sufficiently to receive the acceptance of federal agencies such as the ADA and the FDA. The commercially available dentifrice containing triclosan is produced by the Colgate Palmolive Company. Total toothpaste has been developed by taking a known antimicrobial, triclosan, a phenolic compound that had been used in shampoos and deodorants, and linking it to an agent that allows it to bind to oral tissues. Three major industrial companies, Procter and Gamble, Unilever and Colgate Palmolive Company were all pursuing triclosan as an agent of possible effectiveness in the oral cavity at almost the same point in time. Each company had its own strategy that was designed to make the active agent, triclosan, bind to oral tissues so that it would be active against tooth binding oral microorganisms. To reiterate triclosan on its own did not bind to oral tissues and thus was ineffective in the oral cavity in spite of its potent antimicrobial properties. The Colgate Palmolive Company mixed igicare or gantrex with triclosan to form a polymeric compound that when delivered to the oral cavity bound in such a way as to make the triclosan effective. This combination product, in addition to products containing chlorhexidine, and other agents containing phenolic compounds, are among the only effective agents developed in the last 40 years.

Caries is the single most common chronic childhood disease, five times more common than asthma. Over 70% of children over 17 years old have cavities. Over 108 million Americans lack dental health insurance so that treatment of this infection is lacking. *S. mutans* is considered one of the microbes most associated with dental decay. In studies of children with Localized Juvenile Periodontitis, now known as Localized Aggressive Periodontitis, one of the applicants found that many of these children have minimal decay. Further, these studies found that children with this form of periodontal disease have a variant in a salivary protein, lactoferrin (Lf). When this Lf variant, the lysine variant, was expressed in an insect vector and tested it was found to kill *Streptococcus mutans*. In contrast, another more common Lf variant, the arginine variant, present in healthy non-periodontal disease children had little to no effect on the survival of *S. mutans*.

Recently we have shown that a synthetic peptide with the lysine form of this lactoferrin protein kills *Streptococcus mutans*. Others have shown that lactoferrin peptides have antimicrobial activity, but no one to date has shown that the antibacterial activity derived from this peptide is useful against organisms in the oral cavity. We have also determined that the peptide will have limited usefulness in the oral cavity unless it is linked to something that will allow the peptide to bind to a surface in the oral cavity. A fusion peptide comprising lactoferrin and statherin was previously developed, wherein the lactoferrin portion provided antimicrobial activity while the statherin portion enabled the fusion peptide to adhere to the tooth surface. This fusion peptide is further described in International Application No. PCT/US08/51165, also published as U.S. Publication No. 2010/0144598, each of which is incorporated herein by reference in their entireties. We have now developed a fusion peptide in which the active peptide lactoferrin is linked to a fragment of a *Pseudomonas aeroginosa*-derived fibrillin protein called PAK so that it can both retain its antimicrobial activity and adhere to the buccal epithelial cells (BECs) within the oral cavity to inhibit the growth of bacteria and yeast therein.

Lactoferrin (Lf or LF) is a multifunctional protein that is found in mammary secretion, tears and saliva and in the gastrointestinal tract. Its main function is to sequester iron from its surroundings to prevent oral microbes from attaining iron, a mineral necessary for survival. In addition, in its N-terminus, Lf has a region that has antimicrobial properties. This region is called the defensin region and it has been shown since 1980's that Lf can kill many types of bacteria including oral bacteria. It was also shown that within that N-terminus region, from amino acid position 11 to 31, at least two polymorphic forms exist. For the most part variation in this defensin region at amino acid position 29 can either contain arginine or lysine. As recently as 1998 it has been shown that these two variants in amino acid position 29 have different antimicrobial activities and that peptides designed with those forms could have antimicrobial activity. In fact our group in 2003 produced full length lactoferrin, secreted by insect cells. This insect cell secreted lactoferrin was produced with the two polymorphic forms (lysine and arginine) and was introduced by a baculovirus vector. The secreted protein had all the characteristic properties of human lactoferrin and we tested these two forms for activity against Gram+ and Gram–organisms. We found that the lysine form was more active against a range of Gram+ and Gram–organisms, and specifically more active against *S. mutans*, the reputed cause of dental caries. Since the lysine form of Lf was found more frequently in patients who had Localized Aggressive Periodontitis (LAP), a disease in which the children have less caries than their matched controls, we speculated that this lysine form of lactoferrin may provide an ecological advantage to these children that could explain the reduction in caries seen in these children. Further we then determined that pure lactoferrin would have limited usefulness in the oral cavity unless it was linked to something that would allow it to bind to the oral cavity.

PAK is a Pseudomonas aeroginosa-derived fibrillin protein. It has been determined that a PAK peptide fragment derived from amino acids at the carboxy end of the Pseudomonas pilin protein sequence can adhere to, and subsequently be released from, buccal epithelial cells (BECs). The fragment is a 17-mer with the sequence KCTSDQDEQFIPKGCSK (SEQ ID NO: 4), representing residue numbers 128-144 of the full PAK protein. However it will be appreciated that other fragments of the full-length PAK protein, or the full-length PAK protein itself, may also provide the desired functionality. This ability to adhere to and release from an oral cavity surface makes it an ideal candidate for use in fusion peptides for oral health care.

Described herein is a fusion peptide comprising both lactoferrin and PAK. The fusion peptide has been shown to be effective against a wide spectrum of Gram negative and positive bacteria, as well as yeast. The fusion peptide has also been demonstrated as being capable of binding to BECs and releasing from BECs into the oral cavity to kill bacteria and yeast.

SUMMARY OF THE INVENTION

The present invention is directed to the treatment of dental diseases caused by oral bacteria using Lactoferrin and PAK fusion peptides, and compositions comprising the same.

In certain embodiments, the present invention is directed to a composition for inhibiting the growth of bacteria and/or yeast in the oral cavity comprising a fusion peptide comprising a lysine form of a Lactoferrin polypeptide or a functionally equivalent peptide molecule thereof and a PAK polypeptide or a functionally equivalent peptide molecule thereof.

In other embodiments, the present invention is directed to a fusion peptide having SEQ ID NO: 5, or a functionally equivalent peptide molecule thereof. In yet other embodiments, the present invention is directed to a composition comprising a fusion peptide having SEQ ID NO: 5, or a functionally equivalent peptide molecule thereof. In further embodiments, the present invention is directed to a nucleic acid molecule which encodes the fusion peptide of the present invention.

In further embodiments, the present invention is directed to a method for inhibiting the growth of bacteria and/or yeast in the oral cavity, the treatment or prevention of dental caries, the treatment or prevention of periodontal disease, the treatment or prevention of dental plaque or treating inflammation of the oral cavity associated with the presence of dental plaque by administering an effective amount of a composition comprising a fusion peptide comprising a lysine form of a Lactoferrin polypeptide or a functionally equivalent peptide molecule thereof; and a PAK polypeptide or a functionally equivalent peptide molecule thereof to a patient in need.

In further embodiments, the present invention is directed to a composition comprising a PAK-LF fusion peptide as described herein and the STAT-LF fusion peptide described in International Application No. PCT/US08/51165. In further embodiments, the present invention is directed to a composition comprising a PAK-LF fusion peptide as described herein and a Statherin peptide. In some embodiments, the Statherin peptide is a full-length Statherin peptide. In other embodiments, the Statherin peptide is a fragment of the full-length Statherin peptide.

DETAILED DESCRIPTION OF THE INVENTION

The present invention relates to compositions for inhibiting bacterial and/or yeast colonization. For the purposes of this invention, the term "inhibiting" means reducing or causing the death of existing bacteria and/or yeast, or impeding new bacterial or yeast growth. The invention is also for an oral therapeutic treatment which will inhibit bacterial and yeast colonization in the oral cavity thus reducing the quantity of dental plaque and caries, as well as yeast infections.

One embodiment of the invention is a substantially purified fusion peptide comprising Lactoferrin and PAK (PAK-LF). Exemplary amino acid sequences for PAK-LF are provided in Table 1. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins and/or peptides in the composition. In certain embodiments, the protein or peptide of the invention may be operatively linked to a second peptide sequence.

TABLE 1

Summary of peptides

| Peptide | # of Residues | Net charges | THR (%) | # of THRSS | BI (Kal/mol) | pI | MW |
|---|---|---|---|---|---|---|---|
| LF (lys form) SEQ ID NO: 1 | 11 | +4 | 36 | 3 | 5.12 | 12.7 | 1549 |
| ST SEQ ID NO: 2 | 6 | −4 | | | 7.55 | 3.4 | 750 |
| ST-LF SEQ ID NO: 3 | 17 | 0 | 23 | 3 | 5.98 | 7.2 | 2281 |
| PAK SEQ ID NO: 4 | 17 | 0 | 23 | β st. | 2.93 | 6.3 | 1914 |
| PAK-LF SEQ ID NO: 5 | 28 | +4 | 28 | β st | 3.79 | 10.2 | 3445 |

Table 1 summarizes properties of Lactoferrin (LF), Statherin (ST), and PAK proteins, and fusion peptides comprising combinations thereof. The ST-LF fusion peptides are further disclosed in International Application No. PCT/US08/51165, which is incorporated herein by reference in its entirety. The Bomen Index (BI), is an estimate of the potential of peptides to bind to other proteins and is the sum of the free energies of the reside side chains divided by the total number of residues. THR is the total hydrophobic residues. THRSS is the total hydrophobic residues on the same surface. The ST-LF fusion peptide was previously demonstrated to bind to tooth enamel surfaces. The PAK-LF fusion peptide disclosed herein has been demonstrated to bind to BECs.

Certain embodiments of the invention include amino acid sequences that are functional equivalents of all or part of the PAK-LF sequence. Functionally equivalent amino acid sequences are sequences that encode peptides having the same or similar PAK-LF activity as the PAK-LF peptide as shown in Table 1. The term "PAK-LF activity" as used herein means a peptide that is capable of binding to BECs and that inhibits bacterial and/or yeast colonization. Functionally equivalent amino acid sequences can encode peptides that contain a region having sequence identity to a region of a PAK-LF peptide or more preferably to the entire PAK-LF peptide. Fragments and variants of PAK-LF encompassed by the present invention should preferably have at least about 40%, 60%, 80% or 95% sequence identity to the PAK-LF sequence described in Table 1.

It is also intended that the present invention encompass all nucleic acid molecules encoding the amino acid sequences disclosed herein. Since the genetic code is degenerate, there may be more than one nucleic acid sequence encompassed by the present invention, i.e., more than one nucleic acid sequence will encode a peptide having PAK-LF activity. Certain embodiments of the invention include nucleic acid molecules that are functional equivalents of all or part of the nucleic sequences of the present invention. Nucleic acid molecules (including RNA) having one or more nucleic acid changes compared to the sequences described in this application and which result in production of a peptide disclosed herein are within the scope of various embodiments of the invention.

A nucleic acid molecule may also be referred to as a DNA sequence, nucleic acid sequence, or nucleotide sequence in this application. All these terms have the same meaning as nucleic acid molecule. Functionally equivalent nucleic acid molecules are DNA and RNA (including, without limitation, genomic DNA, complementary DNA, synthetic DNA, and messenger RNA molecules) that encode peptides having the same or similar activity as the PAK-LF peptide of the present invention. Functionally equivalent nucleic acid molecules can encode peptides that contain a region having sequence identity to a region of the PAK-LF peptide, or more preferably, to the entire PAK-LF peptide. Mutations described in this application preferably do not disrupt the reading frame of the coding sequence. Nucleic acid molecules functionally equivalent to the PAK-LF sequences can occur in a variety of forms as described below.

Nucleic acid molecules may encode conservative amino acid changes to PAK-LF peptide. Certain embodiments of the invention include functionally equivalent nucleic acid molecules that encode conservative amino acid changes within a PAK-LF amino acid sequence and produce silent amino acid changes in PAK-LF.

Nucleic acid molecules may encode non-conservative amino acid substitutions, additions or deletions in PAL-LF peptides. Some embodiments of the invention include functionally equivalent nucleic acid molecules that make non-conservative amino acid changes within the PAK-LF amino acid sequence. Functionally equivalent nucleic acid molecules include DNA and RNA that encode peptides and proteins having non-conservative amino acid substitutions (preferably substitution of a chemically similar amino acid), additions, or deletions but which also retain the same or similar PAK-LF activity as the PAK-LF peptide. The DNA or RNA can encode fragments and variants as identified by assays as described below. Fragments and variants of PAK-LF encompassed by the present invention should preferably have at least about 40%, 60%, 80%, or 95% sequence identity to the PAK-LF nucleic acids that encode the molecule, or a region of the sequence, such as the coding sequence or one of the conserved domains of the nucleic acid molecule.

Nucleic acid molecules functionally equivalent to the PAK-LF molecule of the present invention will be apparent from this specification. For example, the nucleic acid sequences of the present invention may have their lengths altered by natural or artificial mutations such as partial nucleotide insertion or deletion, so that when the entire length of the coding sequence is taken as 100%, the functional equivalent nucleic acid molecule preferably has a length of about 60-120% thereof, more preferably about 80-110% thereof. Fragments may be less than 60%.

Nucleic acid molecules containing partial (usually 80% or less, preferably 60% or less, more preferably 40% or less of the entire length) natural or artificial mutations so that some codons in these sequences code for different amino acids, but wherein the resulting peptide retains the same or similar PAK-LF activity. The mutated DNAs created in this manner should preferably encode a peptide having at least about 40%, preferably at least about 60%, at least about 80%, and more preferably at least about 90% or 95% sequence identity to the amino acid sequences contained herein.

Other functional equivalent forms of PAK-LF encoding nucleic acids can be isolated using conventional DNA-RNA or DNA-RNA hybridization techniques. Thus, certain embodiments of the present invention also include nucleic acid molecules that hybridize to one or more of the nucleic acid sequences of the present invention, or any complementary sequences, and that concede expression for peptides and proteins exhibiting the same or similar activity as the PAK-LF peptide of the present invention. Such nucleic acid molecules preferably hybridize to the nucleic acid sequences encompassed by the present invention under moderate to high stringency conditions. High stringency washes have low salt (preferably about 0.2% SSC), and low stringency washes have high salt (preferably about 2% SSC). A temperature of about 37° C. or about 42° C. is considered low stringency, and a temperature of about 50-65° C. is considered high stringency. Some embodiments of the invention also include a method of identify nucleic acid molecules encoding PAK-LF activator peptide (preferably a mammalian peptide), including contacting a sample containing nucleic acid molecules including all or part of the nucleic acids of the present invention, preferably at least about 15-20 nucleotides) under moderate or high stringency conditions and identifying nucleic acid molecules that hybridize to the nucleic acid molecules encompassed by the present invention.

Certain embodiments also include methods of using all or part of the nucleic acid molecules that hybridize to all or part of the nucleic acid sequences encompassed by the present invention, for example, as probes or in assays to identify antagonists or inhibitors of the peptides encompassed by the present invention. Some embodiments of the present invention include methods of using nucleic acid molecules having sequence identity to the PAK-LF nucleic acid sequences described herein in similar methods.

Certain embodiments of this invention also include a nucleic acid molecule kit, including, preferably, in a suitable container or means or attached to a surface, a nucleic acid molecule as disclosed herein, or a peptide having PAK-LF activity and a detection reagent (such as a detection label).

Pharmaceutical Compositions and Methods of Treatment

PAK-LF is also useful when combined with a carrier in a pharmaceutical composition. The compositions are, for example and without limitation, useful when administered in methods of medical treatment or prophylaxis of a disease, disorder or abnormal physical state caused by *S. mutans* or *C. albicans*. Certain embodiments of the invention also include methods of medical treatment of a disease, disorder or abnormal physical state characterized by excessive *S. mutans* or *C. albicans*, for example by administering a pharmaceutical composition including a carrier and PAK-LF. Caries is one example of a disease, which can be treated or prevented by administering PAK-LF. The compositions are also useful when administered in methods of medical treatment or prophylaxis of a disease, disorder or abnormal physical state caused by other dental plaque causing Gram+ or Gram− bacteria including but not limited to *Actinomyces* spp. and other *Streptococci* spp.

Pharmaceutical compositions can be administered to humans or animals by methods such as food, food additives, dentifrices, gels, toothpaste, mouthwash, aerosol spray, pump spray, dental floss, denture wash, denture adhesives, chewing gum, candies, biscuits, soft drinks or sports drinks in methods of medical treatment. PAK-LF may be coupled to lipids or carbohydrates. This increases their ability to adhere to surfaces in the oral cavity, either by prolonging the duration of the adhesion or by increasing its affinity, or both. They may also be coupled to polymers, for example in dental work (e.g. crowns, braces, fillings) or dental floss. Pharmaceutical compositions can be administered to humans or animals. Dosages to be administered depend on individual patient condition, indication of the drug, physical and chemical stability of the drug, toxicity of the desired effect and the chosen route of administration (Robert Rakel, ed., Conn's Current Therapy (1995, W.B. Saunders Company, USA). Pharmaceutical compositions are used to treat diseases caused by dental plaque forming bacterial infections such as dental caries, periodontal disease and endocarditis. In a preferred embodiment, the pharmaceutical compositions are used to treat diseases caused by *Candida* spp, *Actinomyces* spp. and *Streptococci* spp.

In a preferred embodiment, pharmaceutical compositions according to the invention are prepared using one or more PAK-LF peptides capable of inhibiting bacterial and/or yeast growth within the oral cavity.

Pharmaceutical compositions comprising PAK-LF peptides are particularly useful for methods of treatment or prevention (prophylaxis) of a disease, disorder or abnormal physical state caused by bacterial and yeast infection.

Pharmaceutical compositions can be prepared by known methods for the preparation of pharmaceutically acceptable compositions which can be administered to patients, and such that an effective quantity of the fusion peptide is combined in a mixture with a pharmaceutically acceptable vehicle. Suitable carriers are described, for example in Remington's Pharmaceutical Sciences (Remington's Pharmaceutical Sciences, Mack Publishing Company, Easton, Pa., USA). Carriers include saline and D5W (5% dextrose and water). Excipients include additives such as a buffer, solubilizer, surfactant, suspending agent, emulsifying agent, viscosity controlling agent, flavor, lactose filler, antioxidant, preservative or dye. There are preferred excipients for stabilizing peptides for parenteral and other administration. The excipients include serum albumin, glutamic or aspartic acid, phospholipids and fatty acids.

The present invention further encompasses a composition comprising the PAK-LF fusion peptide in combination with the ST-LF fusion peptide (and/or functionally equivalent fragments thereof) disclosed in International Application No. PCT/US2008/51165, incorporated herein by reference in its entirety. The present invention further encompasses a composition comprising the PAK-LF fusion peptide of the present in combination with a full length statherin peptide, and/or fragments thereof.

In the compositions of the present invention, the PAK-LF and/or ST-LF fusion peptide may be pegylated. In certain embodiments, the PAK or ST portion of the peptide is pegylated. In other embodiments, the LF portion of the peptide is pegylated.

In other preferred embodiments, surfactants are included in the compositions. The surfactants which may be used in the present invention generally include pharmaceutically acceptable anionic surfactants, cationic surfactants, amphoteric (amphipathic/amphophtlic) surfactants, and non-ionic surfactants. Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates (including docusate sodium or dioctyl sodium succinate (DSS)), alpha olefin sulfonates, and phosphated ethoxylated alcohols. Suitable pharmaceutically acceptable cationic surfactants include, for example, monoalkyl quaternary ammonium salts, dialkyl quaternary ammonium compounds, amidoamines, and aminimides. Suitable pharmaceutically acceptable amphoteric (amphipathic/amphophilic) surfactants, include, for example, N-substituted alkyl amides, N-alkyl betaines, sulfobetaines, and N-alkyl β-aminoprorionates.

In preferred embodiments, sodium lauryl sulfate is used. In even more preferred embodiments, the composition comprises from about 0.1 to about 10%, from about 0.3 to about 5% or from about 0.5% to about 2% by volume of sodium lauryl sulfate. Alternatively, a substituted sequence on one of the lysine residues that embodies activities that convey activities like sodium lauryl sulfate may be inserted into the fusion peptide. For example, the side chain of Lys may be modified with undecanoic acid: this will introduce a long alkyl chain similar to the dodecyl moiety in SLS.

The side chain of Lys may also be modified with aminoundecanoic acid: this will introduce a long alkyl chain similar to the dodecyl moiety in SLS and a positive charge ($NH_2$) at the end.

The side chain Lys may also be modified, for example, with aminoundecanoic acid and couple aspartic acid at the end to introduce a zwitter ion at the end.

On this basis, pharmaceutical compositions could include an active compound or substance, such as a PAK-LF peptide, in association with one or more pharmaceutically acceptable vehicles or diluents, and contained in buffered solutions with a suitable pH and isoosmotic with the physiological fluids. A pharmaceutical carrier will depend on the intended route of administration. Methods of combining the active molecules with the vehicles or combining them with diluents are well known to those skilled in the art. Compositions may also contain additives such as antioxidants, buffers, bacteriostatis, bactericidal antibiotics and solutes which render the formulation isotonic in the intended recipient; and aqueous and non-aqueous sterile suspensions which may include suspending agents and thickening agents. The composition could include a targeting agent for the transport of the active compound to specified sites.

Pharmaceutical compositions according to the invention can be administered by any suitable route known in the art. In cases where the infection is localized, the pharmaceutical composition can be administered topically to infected area. In cases where the infection is systemic, the pharmaceutical composition may be administered orally, intravenously, or parenterally.

In some instances, it may be desirable to administer the pharmaceutical compositions according to the invention with a known antibacterial or anti-Candidal agent, such as an antibiotic or an antifungal. In some instances, the pharmaceutical compositions which repress biofilm formation are also useful for rendering the bacterial cells more susceptible to antibiotics. In further instances, the compositions of the present invention are used for the treatment of dry mouth.

The term "antibiotic" as used herein refers to any compound known to one of ordinary skill in the art that will inhibit the growth of, or kill, bacteria. The term "antibiotic" includes, but is not limited to, beta-lactams (penicillins and cephalosporins), vancomycins, bacitracins, macrolides (erythromycins), lincosamides (clindomycin), chloramphenicols, tetracyclines, aminoglycosides (gentamicins), amphotericins, cefazolins, clindamycins, mupirocins, sulfonamides and trimethoprim, rifampicins, metronidazoles, quinolones, novobiocins, polymixins, gramicidins or any salts or variants thereof. The antibiotic used will depend on the type of bacterial infection.

A therapeutically effective dosage of the pharmaceutical compositions according to the invention will depend on the type and severity of the infection and whether the pharmaceutical composition comprises a further active ingredient such as an antibiotic. Generally, the therapeutically effective dose is the minimal amount sufficient for controlling biofilm formation or dental caries and which is not toxic to the human or animal treated. Methods for determining effective dosages and toxicity are known in the art.

A further aspect of the present invention provides the use in the preparation of a medicament for administration to a mammalian patient to improve oral health or to alleviate dental caries, of viable, transfected cells genetically modified to produce PAK-LF peptides which inhibits the growth of bacteria and or yeast in the oral cavity.

Pharmaceutical Compositions

PAK-LF peptides described above for use in the preparation of pharmaceutical compositions can also be used to prepare antimicrobial and antifungal compositions such as a liquid disinfecting solution. Such solutions may further comprise antimicrobials or antifungals such as alcohol, povidone-iodine solution and antibiotics as well as preservatives. These solutions can be used, for example, as disinfectants of the skin or surrounding area prior to insertion or implantation of a device such as a catheter, as catheter lock and/or flush solutions, and as antiseptic rinses for any medical device including, but not limited to catheter components such as needles, Leur-Lok connectors, needleless connectors and hubs as well as other implantable devices. These solutions can also be used to coat or disinfect surgical instruments including, but not limited to, clamps, forceps, scissors, skin hooks, tubing, needles, retractors, scalers, drills, chisels, rasps and saws.

Antimicrobial compositions may comprise any of the peptide, antisense and antibody PAK-LF peptides described above.

An antimicrobial composition may further comprise additional ingredients including but not limited to: a surfactant, an antiseptic and an antibiotic (see examples listed above).

Production of PAK-LF by Chemical Synthesis and in Eukaryotic and Prokaryotic Cells The fusion peptides described herein, particularly those having relatively short sequences, can be produced according to general chemosynthetic methods. For example, either a conventionally known solid-phase synthetic method or liquid-phase synthetic method can be used. A solid-phase synthetic method using Boc (t-butyloxycarbonyl) or Fmoc (9-fluorenylmethoxycarbonyl) as a protective group for the amino group is preferable. In certain embodiments, the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is one method for the chemical synthesis of the peptides of the invention. It is noted that in the chemical synthesis of peptides, the synthesis may produce a number of truncated peptides in addition to the desired full-length product. Thus, the peptides are typically purified using, e.g., HPLC.

A polynucleotide provided by the present invention may be in the form of DNA or RNA (mRNA or the like). The DNA can be provided in the form of a double strand or a single strand. When provided in the form of a single strand, it may be in the form of a code chain (sense chain) or may be non-code chain (anti-sense chain) that is complementary thereto. The polynucleotide provided by the present invention can be used as a material for constructing a recombinant gene for producing a fusion peptide in various host cells.

Nucleic acid molecules encoding the fusion peptides disclosed herein may be obtained from a cDNA library. Nucleotide molecules can also be obtained from other sources known in the art such as expressed sequence tag analysis or in vitro synthesis. The DNA (including variants that are functional equivalents) can be introduced into and expressed in a variety of eukaryotic and prokaryotic host cells. A recombinant nucleic acid molecule for the PAK-LF contains suitable operatively linked transcriptional or translational regulatory elements. Suitable regulatory elements are derived from a variety of sources, and they may be readily selected by one with ordinary skill in the art (Sambrook, J, Fritsch, E. E. & Maniatis, T. (Most Recent Edition). Molecular Cloning: A Laboratory Manual. Cold Spring Harbor Laboratory Press. New York; Ausubel et al. (Most Recent Edition). Current Protocols in Molecular Biology, John Wiley & Sons, Inc.). For example, if one were to upregulate the expression of the nucleic acid molecule, one could insert a sense sequence or silencing RNA and the appropriate promoter into the vector. Promoters can be inducible or constitutive, environmentally- or developmentally-regulated, or cell- or tissue-specific. Transcription is enhanced with promoters known in the art for expression. CMV and SV40 promoters are commonly used to express desired peptide in cells. Other promoters known in the art may also be used (many suitable promoters and vectors are described in the applications and patents referenced in this application).

If one were to downregulate the expression of the nucleic acid molecule, one could insert the antisense sequence and the appropriate promoter into the vehicle. A nucleic acid molecule may be either isolated from a native source (in sense or antisense orientations), synthesized, or it may be a mutated native or synthetic sequence or a combination of these.

Examples of regulatory elements include a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. Other regulatory regions that may be used include an enhancer domain and a termination region. Regulatory elements may bacterial, fungal, viral or avian in origin. Likewise regulatory elements may originate from animal, plant, yeast, insect or other sources, including synthetically produced elements and mutated elements.

In addition to using expression vectors described above, a peptide may be expressed by inserting a recombinant nucleic acid molecule in a known expression system derived from bacteria, viruses, yeast, mammals, insects, fungi or birds. A recombinant molecule may be introduced into cells by techniques such as Agrobacterium tumefaciens-mediated transformation, particle-bombardment-mediated transformation, direct uptake, microinjection, coprecipitation, transfection and electroporation depending on the cell type. Retroviral vectors, adenoviral vectors, Adeno Associated Virus (AAV) vectors, DNA virus vectors and liposomes may be used. Suitable constructs are inserted in an expression vector, which may also include markers for selection of transformed cells. A construct may be inserted at a site created by restriction enzymes.

In one embodiment of the invention, a cell is transfected with an expression vector containing a nucleic acid molecule encoding the fusion peptide of the invention to produce cells expressing a peptide encoded by the nucleic acid molecule.

Another embodiment of the invention relates to a method of transfecting a cell with a nucleic acid molecule encoding the fusion peptide disclosed herein, inserted in an expression vector to produce a cell expressing the PAK-LF peptide or other peptide of the invention. In accordance with certain embodiments of the invention a method is provided for expressing the disclosed peptides in a cell. A preferred process would include culturing a cell including a recombinant DNA vector including a nucleic acid molecule encoding PAK-LF in a culture medium so that the peptide is expressed. The process preferably further includes recovering the peptide from the cells or culture medium.

Probes

Certain embodiments of the present invention include oligonucleotide probes. The probes are useful to identify nucleic acids encoding PAK-LF peptides, as well as peptides functionally equivalent to PAK-LF. The oligonucleotide probes are capable of hybridizing to the nucleic acid sequence encoding the fusion peptide of the invention under stringent hybridization conditions. A nucleic acid molecule encoding a peptide disclosed herein may be isolated from other organisms by screening a library under moderate to high stringency hybridization conditions with a labeled probe. The activity of the peptide encoded by the nucleic acid molecule is assessed by cloning and expression of the DNA. After the expression product is isolated, the peptide is assayed for PAK-LF activity.

Functionally equivalent PAK-LF peptide molecules from other cells, or equivalent PAK-LF-encoding cDNAs or synthetic DNAs, can also be isolated by amplification using Polymerase Chain Reaction (PCR) methods. Oligonucleotide primers, such as degenerate primers, can be prepared and used with PCR and reverse transcriptase (E. S. Kawasaki (1990), In Innis et al., Eds., PCR Protocols, Academic Press, San Diego, Chapter 3, p. 21) to amplify functional equivalent DNAs from genomic or cDNA libraries of other organisms. Oligonucleotides can also be used as probes to screen cDNA libraries.

Functionally Equivalent Peptides and Proteins

The present invention includes not only peptides encoded by the sequences disclosed herein, but also functionally equivalent peptides and proteins that exhibit the same or similar PAK-LF peptide activity as wells as mimetics, and nucleic acid sequences encoding the same.

EXAMPLES

Example 1

BEC Binding Assay

PAK and PAK-LF peptides were incubated with BECs to assess the fusion peptide's ability to bind to BECs. Each peptide was incubated either with or without BECs for 30 minutes at room temperature, and then washed with PBS. After washing, 100 μL aliquots containing the peptides were applied to wells and subjected to dot blot analysis according to the manufacturer's protocol (Bio-Rad). Different LF antibody was used to detect the LF peptides to check sensitivity to each peptide.

Figure 1:
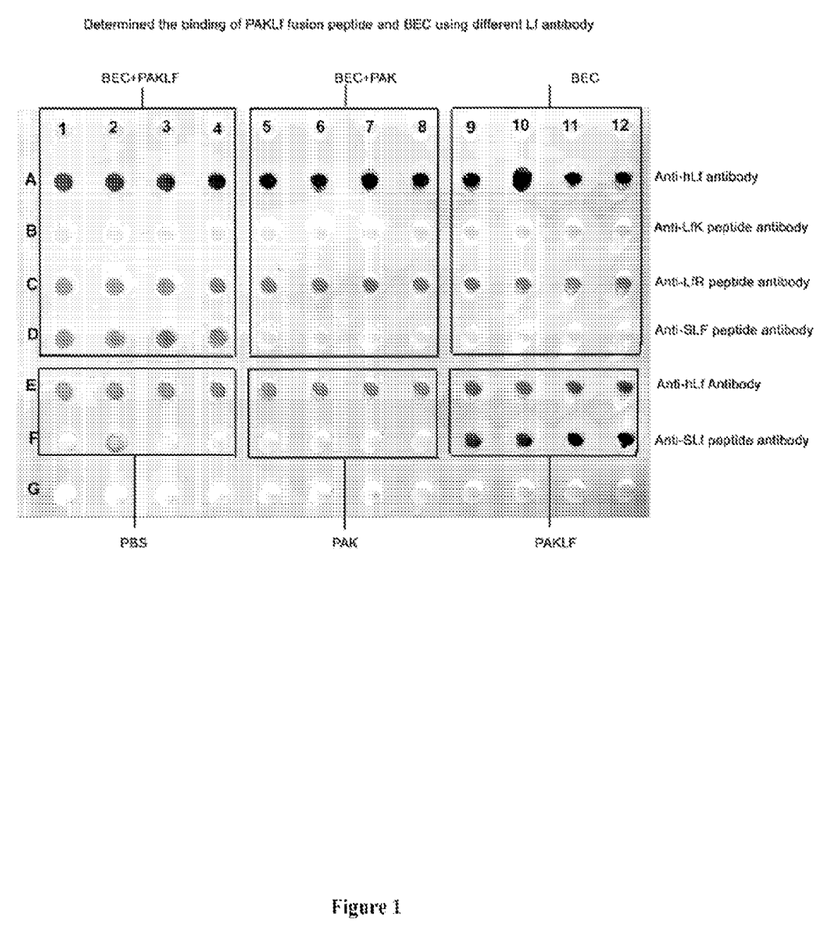
FIG. 1 depicts the binding of the LF-PAK fusion peptide to BECs using different LF antibodies by dot blot analysis. For rows A-D, columns 1-4 contain BEC+PAK-LF peptide, columns 5-8 contain BEC-PAK, and column 9-12 contains BEC only. For rows E-F, rows 1-4 contain PBS only, rows 5-8 contain PAK only, and rows 9-12 contain PAK-LF only.
Figure 2:
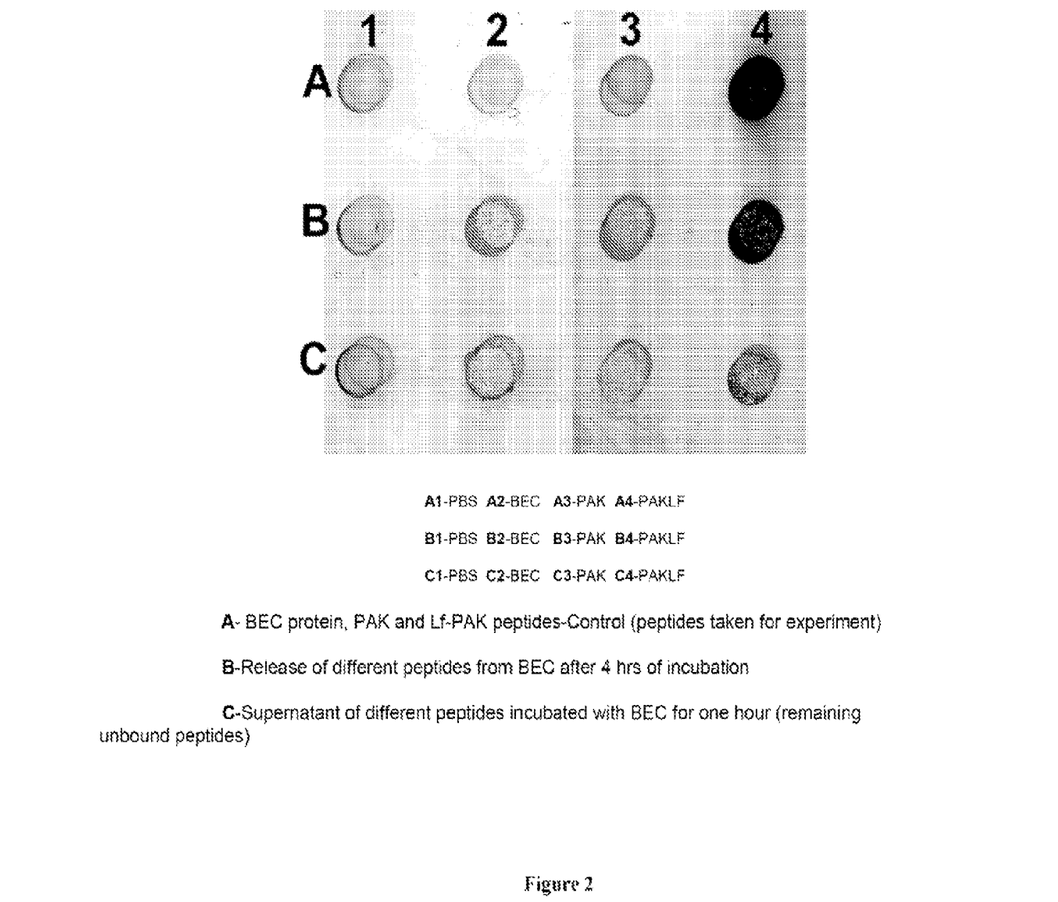
FIG. 2 depicts the substantivity of the LF-PAK fusion peptide after BEC incubation. Row A is the control lane containing BEC protein, PAK and LF-PAK peptides. Row B depicts the release of different peptides from BECs after 4 hours of incubation. Row C depicts the supernatant of different peptides incubated with BECs for one hour (i.e., the remaining unbound peptides).

FIG. 1 depicts the resulting blot, which demonstrates the binding of PAK-LF to BECs using different LF antibody. The results show that the PAK-LF fusion peptide binds BECs and that the SLf antibody recognized only the PAK-LF fusion peptide. FIG. 2 depicts the substantivity of the PAK-LF fusion peptide after BEC incubation. It was estimated that 527 μg/mL of LF fusion peptide was incubated with BEC for one hour (i.e., the initial concentration of peptide). It was estimated that 275 μg/mL of peptide was measured from the unbound solution after one hour. It was estimated that 118 μg/mL of peptide was released from the BECs after 4 hours, and that 134 μg/mL of peptides may have been retained by the BECs after 4 hours. This example demonstrates that the PAK-LF fusion peptide binds to BECs and is then slowly released from the BECs.

Example 2

Anti-*Candida* Activity of PAK-LF Fusion Peptide

To determine the minimum inhibitory concentration of fusion peptide, PAK-LF was incubated with *Candida albicans* for 2 hours at 37° C. The cells were then washed with PBS. The cells were then serially diluted and plated on Sabouraud dextrose agar, and the colonies were counted after 2 days of incubation at 37° C.

Figure 3:
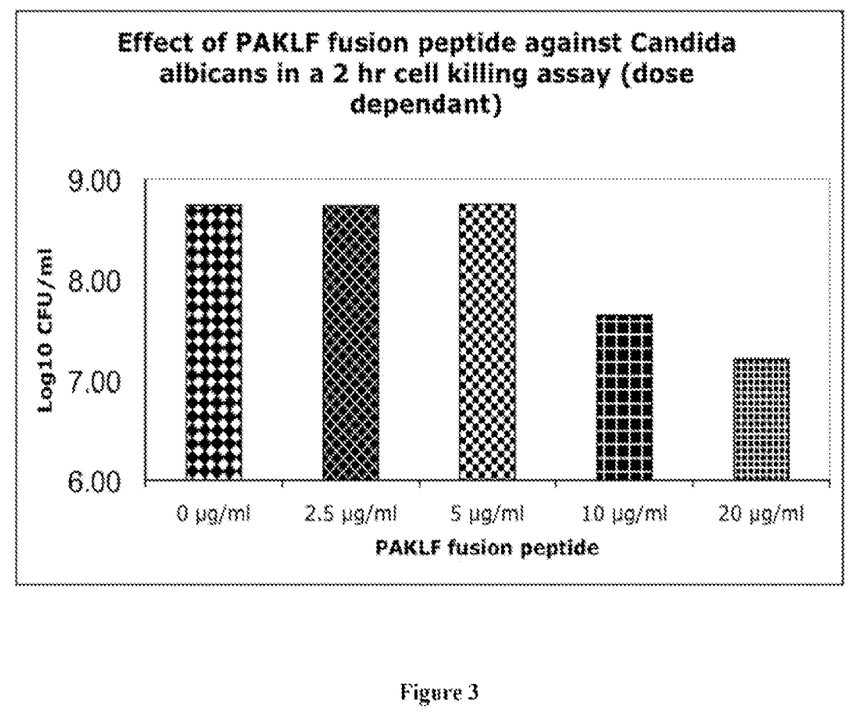
FIG. 3 depicts the effect of PAK-LF fusion peptide against *Candida albicans* in a 2 hour killing assay (dose dependent).

The results are shown in FIG. 3. The results show, e.g., that 20 μg/mL of fusion peptide inhibits *C. albicans* approximately 1.5 of Log 10 CFU/mL, whereas at 5 μg/mL, there was no inhibition observed.

Figure 4:
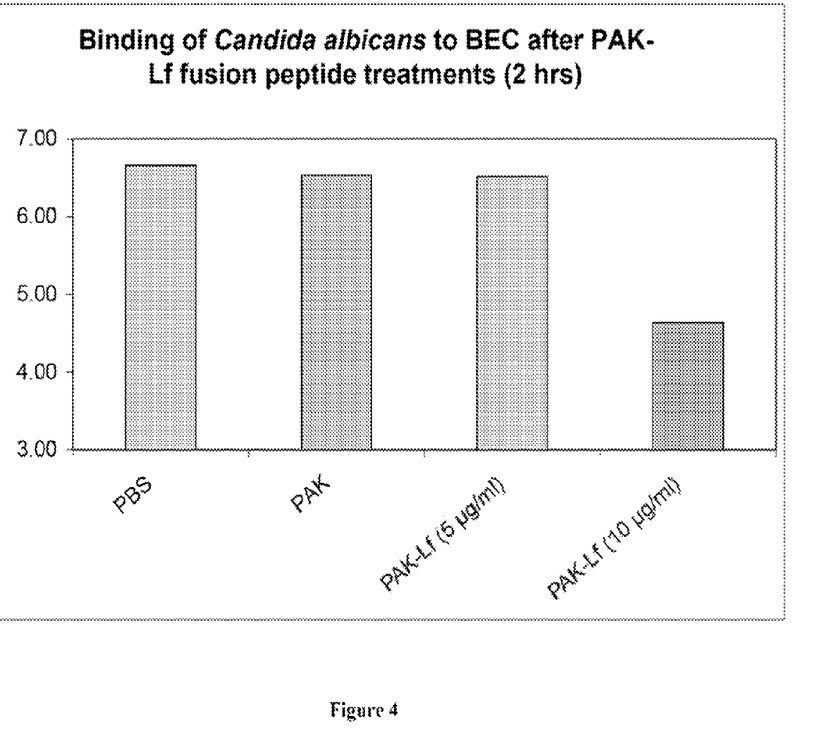
FIG. 4 depicts the binding of *Candida albicans* to BEC after PAK-LF fusion peptide treatments for 2 hours.

The peptides were further incubated with BECs at various concentrations (5 and 10 μg/mL) for 30 minutes, along with a control comprising no peptide. The cells were then washed with PBS. The BECs were then incubated with *C. albicans* for 2 hours in a binding assay. After 2 hours, the BECs were placed on Ficoll gradient and centrifuged at slow speed and plated on to Sabouraud dextrose agar plates. The results (FIG. 4) show that PAK-LF at 10 μg/mL of peptide inhibited the growth of *Candida*.

Example 3

Figure 5:
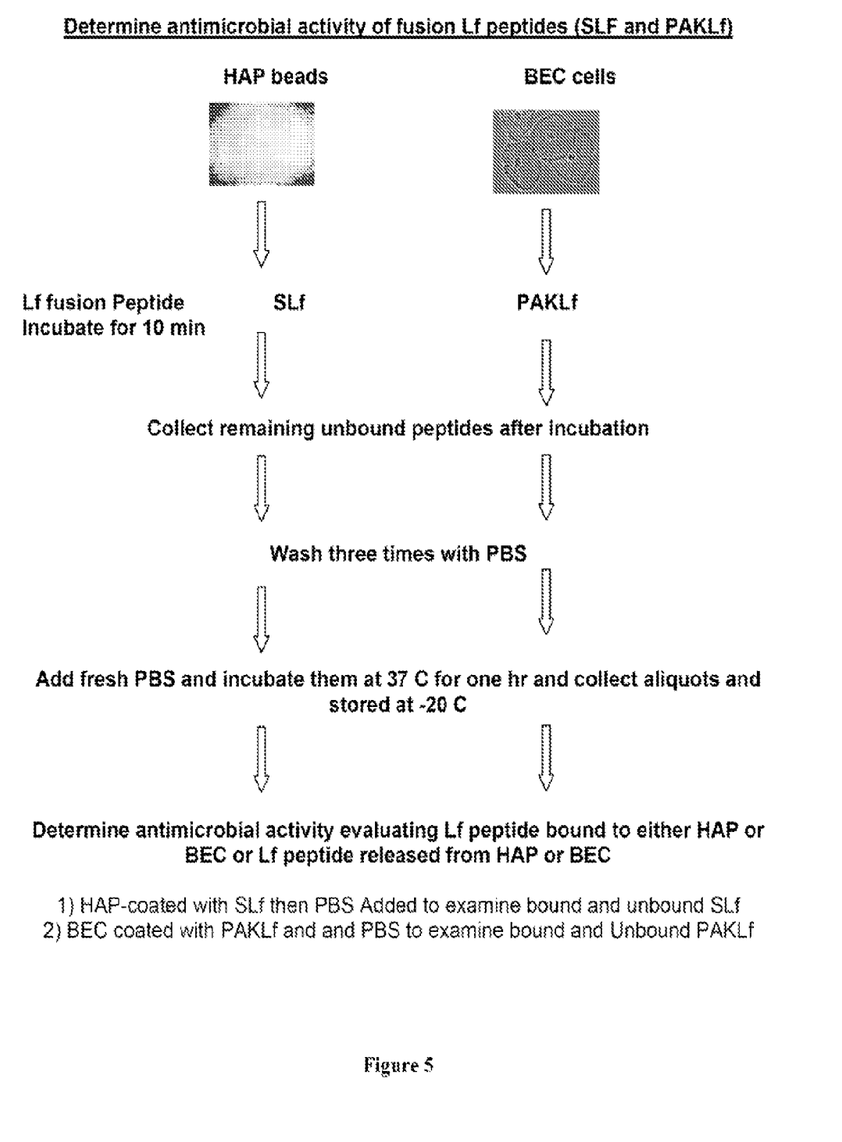
FIG. 5 depicts the process by which antimicrobial activity of various LF fusion peptides was determined.
Figure 6:
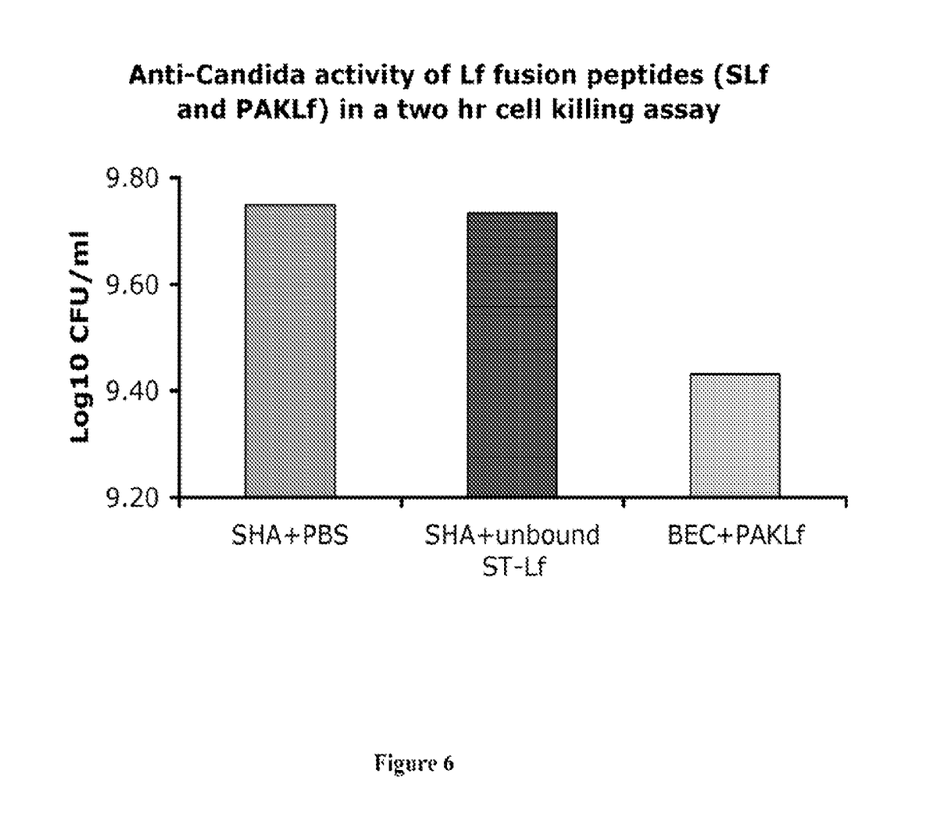
FIG. 6 depicts the anti-*Candida* activity of LF fusion peptides (ST-LF and LF-PAK) in a 2 hour killing assay.

Anti-*Candida* Activity of LF Fusion Peptides (ST-LF and PAK-LF) in a Two Hour Cell Killing Assay with Salivary-Coated HAP The procedures depicted in FIG. 5 were carried out with two LF fusion peptides (ST-LF and PAK-LF). Salivary-coated HAP was incubated with ST-LF peptide for 30 minutes and then washed with PBS and the supernatant tested. Fresh PBS was added, and the salivary-coated HAP was further incubated for 1 hour. The salivary-coated HAP was again rinsed and the supernatant solution was then tested for anti-candidal activity. The results are depicted in FIG. 6. Based on the 2 hour cell killing assay, no inhibition of *Candida* indicated that the peptide was not released from the sHAP, as was expected. On the other hand, fusion peptide PAK-LF and ST-LF+PAK-LF incubated with BECs show that there was significant inhibition observed in the unbound solution, indicating that the fusion peptide was released from the BECs.

---

PEPTIDE SEQUENCES

SEQ ID NO: 1
FQWQRNMRKVR (LF, lys form)

SEQ ID NO: 2
DDDEEK (Synthetic ST)

SEQ ID NO: 3
DDDEEKFQWQRNMRKVR (ST-LF fusion peptide)

SEQ ID NO: 4
KCTSDQDEQFIPKGCSK (PAK)

SEQ ID NO: 5
KCTSDQDEQFIPKGCSKFQWQRNMRKVR (PAK-LF fusion peptide)

SEQ ID NO: 6:
MKAQKGFTLIELMIVVAIIGILAAIAIPQYQNYVARSEGASALAS

VNPLKTTVEEALSRGWSVKSGTGTEDATKKEVPLGVAADANKLGT

IALKPDPADGTADITLTFTMGGAGPKNKGKIITLTRTAADGLWKC

TSDQDEQFIPKGCSK(Full-length PAK sequence)

---

What is claimed is:

1. A composition for inhibiting bacterial growth in the oral cavity comprising a fusion peptide comprising:
   i. a lysine form of a Lactoferrin polypeptide; and
   ii. a PAK polypeptide,
   wherein the fusion peptide consists essentially of SEQ ID NO: 5.

2. The composition of claim 1, wherein the composition further comprises a pharmaceutically acceptable excipient.

3. The composition of claim 1, wherein the composition further comprises a surfactant molecule.

4. The composition of claim 3, wherein the surfactant is sodium lauryl sulfate.

5. The composition of claim 4, wherein the sodium lauryl sulfate is present in an effective amount to allow the composition to penetrate a biofilm.

6. The composition of claim 2, wherein the composition is a dosage form selected from the group consisting of a food, a food additive, dentifrices, gels, toothpaste, mouthwash, aerosol spray, pump spray, dental floss, denture wash, denture adhesives, chewing gum, candy, chewable tablets and solution.

7. The composition of claim 1, further comprising an antibacterial agent, an antimicrobial agent, an antifungal agent, anti-candidal agent, or a combination thereof.

8. The composition of claim 1, further comprising a statherin polypeptide comprising SEQ ID NO: 2.

9. The composition of claim 1, further comprising a STAT-LF fusion peptide comprising:
   i. a lysine form of a Lactoferrin polypeptide; and
   ii. a Statherin polypeptide.

10. The composition of claim 9, wherein the STAT-LF fusion peptide comprises SEQ ID NO: 3.

11. A fusion peptide consisting essentially of SEQ ID NO: 5.

12. A composition for inhibiting bacterial growth in the oral cavity comprising the fusion peptide of claim 11.

13. A method for inhibiting bacteria and/or yeast in the oral cavity comprising administering an effective amount of the composition of claim 1 to a patient in need thereof.

14. The method of claim 13, wherein the composition further comprises a pharmaceutically acceptable excipient.

15. The method of claim 13, wherein the composition further comprises a surfactant.

16. The method of claim 15, wherein the surfactant is sodium lauryl sulfate.

17. The method of claim 16, wherein the sodium lauryl sulfate is an effective amount to allow the composition to penetrate a biofilm.

18. The method of claim 13, wherein the composition is administered via a dosage form selected from the group consisting of a food, a food additive, dentifrices, gels, toothpaste, mouthwash, dental floss, denture wash, denture adhesives, chewing gum, candy, chewable tablets and solution.

19. The method of claim 13, wherein the composition further comprises an antibacterial agent, an antimicrobial agent, antifungal agent, anti-candidal agent, or a combination thereof.

* * * * *

SEQUENCE LISTING

<160> NUMBER OF SEQ ID NOS: 6

<210> SEQ ID NO 1
<211> LENGTH: 11
<212> TYPE: PRT
<213> ORGANISM: Homo sapiens

<400> SEQUENCE: 1

```
Phe Gln Trp Gln Arg Asn Met Arg Lys Val Arg
1               5                   10

<210> SEQ ID NO 2
<211> LENGTH: 6
<212> TYPE: PRT
<213> ORGANISM: Artificial
<220> FEATURE:
<223> OTHER INFORMATION: Synthetic statherin fragment

<400> SEQUENCE: 2

Asp Asp Asp Glu Glu Lys
1               5

<210> SEQ ID NO 3
<211> LENGTH: 17
<212> TYPE: PRT
<213> ORGANISM: Artificial
<220> FEATURE:
<223> OTHER INFORMATION: ST-LF fusion peptide

<400> SEQUENCE: 3

Asp Asp Asp Glu Glu Lys Phe Gln Trp Gln Arg Asn Met Arg Lys Val
1               5                   10                  15

Arg

<210> SEQ ID NO 4
<211> LENGTH: 17
<212> TYPE: PRT
<213> ORGANISM: Homo sapiens

<400> SEQUENCE: 4

Lys Cys Thr Ser Asp Gln Asp Glu Gln Phe Ile Pro Lys Gly Cys Ser
1               5                   10                  15

Lys

<210> SEQ ID NO 5
<211> LENGTH: 28
<212> TYPE: PRT
<213> ORGANISM: Artificial
<220> FEATURE:
<223> OTHER INFORMATION: PAK-LF fusion peptide

<400> SEQUENCE: 5

Lys Cys Thr Ser Asp Gln Asp Glu Gln Phe Ile Pro Lys Gly Cys Ser
1               5                   10                  15

Lys Phe Gln Trp Gln Arg Asn Met Arg Lys Val Arg
            20                  25

<210> SEQ ID NO 6
<211> LENGTH: 150
<212> TYPE: PRT
<213> ORGANISM: Homo sapiens

<400> SEQUENCE: 6

Met Lys Ala Gln Lys Gly Phe Thr Leu Ile Glu Leu Met Ile Val Val
1               5                   10                  15

Ala Ile Ile Gly Ile Leu Ala Ala Ile Ala Ile Pro Gln Tyr Gln Asn
                20                  25                  30

Tyr Val Ala Arg Ser Glu Gly Ala Ser Ala Leu Ala Ser Val Asn Pro
            35                  40                  45

Leu Lys Thr Thr Val Glu Glu Ala Leu Ser Arg Gly Trp Ser Val Lys
```

```
                50                  55                  60
Ser Gly Thr Gly Thr Glu Asp Ala Thr Lys Lys Glu Val Pro Leu Gly
65                  70                  75                  80

Val Ala Ala Asp Ala Asn Lys Leu Gly Thr Ile Ala Leu Lys Pro Asp
                85                  90                  95

Pro Ala Asp Gly Thr Ala Asp Ile Thr Leu Thr Phe Thr Met Gly Gly
                100                 105                 110

Ala Gly Pro Lys Asn Lys Gly Lys Ile Ile Thr Leu Thr Arg Thr Ala
                115                 120                 125

Ala Asp Gly Leu Trp Lys Cys Thr Ser Asp Gln Asp Glu Gln Phe Ile
                130                 135                 140

Pro Lys Gly Cys Ser Lys
145                 150
```